US009222055B2

(12) United States Patent
Fraser et al.

(10) Patent No.: US 9,222,055 B2
(45) Date of Patent: Dec. 29, 2015

(54) HIGH INTENSITY FRAGRANCES

(75) Inventors: Stuart Fraser, Cheshire (GB); Dominique Gindre, Courbevoie (FR); Jonathan Warr, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 373 days.

(21) Appl. No.: 12/716,392

(22) Filed: Mar. 3, 2010

(65) Prior Publication Data

US 2010/0226871 A1 Sep. 9, 2010

(30) Foreign Application Priority Data

Mar. 4, 2009 (EP) .................................... 09305204
Aug. 31, 2009 (EP) .................................... 09169071

(51) Int. Cl.
*A61L 9/04* (2006.01)
*C11B 9/00* (2006.01)

(52) U.S. Cl.
CPC ................ *C11B 9/0015* (2013.01); *C11B 9/00* (2013.01); *C11B 9/0019* (2013.01); *C11B 9/0034* (2013.01); *C11B 9/0061* (2013.01); *C11B 9/0076* (2013.01)

(58) Field of Classification Search
CPC ........... A61L 9/01; A61L 6/012; A61L 9/014; A61L 9/042; A61L 9/12; A61L 9/048; C11D 17/047; C11D 3/505
See application file for complete search history.

(56) References Cited

U.S. PATENT DOCUMENTS

| | | | | |
|---|---|---|---|---|
| 5,411,992 | A * | 5/1995 | Eini et al. | 514/731 |
| 5,500,154 | A | 3/1996 | Bacon et al. | |
| 6,268,233 | B1 | 7/2001 | Sano | |
| 2002/0137660 | A1 | 9/2002 | Kuhn et al. | |
| 2003/0065213 | A1 | 4/2003 | Zofchak | |
| 2004/0127463 | A1 | 7/2004 | Trinh et al. | |
| 2006/0165622 | A1 * | 7/2006 | Hiramoto et al. | 424/65 |
| 2008/0058738 | A1 * | 3/2008 | Roberts et al. | 604/359 |
| 2008/0207481 | A1 * | 8/2008 | Meine et al. | 512/4 |

FOREIGN PATENT DOCUMENTS

| | | | | |
|---|---|---|---|---|
| EP | 0 299 561 | B1 | 1/1996 | |
| EP | 1 884 251 | A1 | 2/2008 | |
| WO | 96/31590 | A1 | 10/1996 | |
| WO | 97/34987 | A1 | 9/1997 | |
| WO | 99/65458 | A1 | 12/1999 | |
| WO | WO 02089862 | A2 * | 11/2002 | A61L 9/01 |
| WO | 2005/055964 | A1 | 6/2005 | |

OTHER PUBLICATIONS

Partial European Search Report dated Oct. 1, 2009 in Counterpart European application No. 09305204.1.
European Search Report issued on Sep. 8, 2010 in the corresponding European Patent Application No. EP 09169071.

* cited by examiner

*Primary Examiner* — Lezah Roberts
*Assistant Examiner* — Nannette Holloman
(74) *Attorney, Agent, or Firm* — Sughrue Mion, PLLC

(57) ABSTRACT

The present invention relates to a high intensity fragrance composition for use in a cosmetic, toiletry, personal care, personal cleansing product or adsorbent article, which comprises by weight: a) 75% to 100% of at least 2 fragrance ingredients where each fragrance ingredients must contain only atoms of carbon, hydrogen, oxygen and nitrogen, comprise an ester functional group, an alcohol functional group or an aldehyde functional group, have boiling points between 100° C. and 300° C. at a pressure of 760 mm of mercury, have molecular weights within the range of 70 atomic mass units to 175 atomic mass units, and have ClogP values between 0.00 and 4.00; b) 0 to 25% of an essential oil; and c) 0 to 25% of a fragrance ingredient other than the fragrance ingredients in category a), wherein the sum of a), b) and c) equals 100%.

9 Claims, No Drawings

HIGH INTENSITY FRAGRANCES

CROSS-REFERENCE TO RELATED APPLICATIONS

This application claims priority from European Patent Application No. 09 305 204.1 filed on Mar. 4, 2009, and European Patent Application No. 09 169 071.9 filed on Aug. 31, 2009, the entire subject matter of which is incorporated herein by reference.

BACKGROUND OF THE INVENTION

1. Technical Field of the Invention

The invention relates to high intensity fragrance compositions for use in cosmetic, toiletry, personal care and personal cleansing products and adsorbent articles which reduce the amount of fragrance dosed into a product and are preferably hypoallergenic. The fragrance ingredients which comprise the high intensity fragrances predominantly comprise compounds having alcohol, ester or aldehyde functional groups and preferably are sourced from natural raw materials.

2. Background of the Invention

Perfumes in cosmetic, toiletry, personal core and personal cleansing products provide several functions. They mask base odors, provide an olfactory aesthetic benefit and serve as a signal of product attributes and function, e.g. hygiene, cleanliness, mildness etc. Unfortunately, in addition to these benefits, perfumes can also cause difficulties such as problems within products e.g. stickiness in powders, discoloration in soap bars, phase separation in liquid; problems for users e.g. eye irritation and occasionally allergic reaction in certain individuals. Perfumes are also one of the more expensive ingredients in products and many perfume molecules are not very readily biodegradable. Despite these several disadvantages the level of perfume dosed in consumer products has tended to increase over the past 20 years. However consumers have also become more critical of the products they purchase and increasingly they sustainable sources and for fragrance this means that they are derived form vegetable sources and preferably from organically cultivated sources; that they impose less impact on the environment i.e. they are more readily biodegradable and that they meet high human safety standards. These influences drive perfume houses to be more creative in fragrance formulation and in finding new raw materials.

There have been numerous publications which define subsets of perfume ingredients by molecular properties which are particularly suitable for specific applications. Sometimes these selections apply to a whole fragrance and sometimes to part of a fragrance also known as an accord. Selections may depend on chemical reactivity such as the lack of reactivity of certain categories of fragrance ingredients with bleach molecules in products as exemplified in EP 299561 or WO 96/031590. Alternatively the application may define some molecular parameters which can be used as a predictor of a desirable property; so U.S. Pat. No. 5,500,154 defines enduring fragrances characterized by fragrance ingredients having boiling points greater than 300° C. with ClogP values greater than 3.00 and having improved substantively to fabric in laundry applications. WO 97/34987 defines perfumes with ClogP greater than 3.00 and boiling points below 260° C. which bloom when in use in automatic dishwashing applications. The selection may also depend on a measured parameter such as an odor detection threshold. For example, WO 99/65458 defines two categories of fragrance ingredients to be formulated into high impact accords based on a combination of boiling point, partition coefficient (ClogP) and measured odor detection thresholds. These accords can be optionally encapsulated in starch to provide a boost of fragrance from a detergent powder when dispersed in water.

The present invention changes the conventional fragrance formulation which combines top notes, mid notes and base notes to create a fragrance. The terms top notes, mid notes and base notes are well understood by those skilled in perfume creation. See "The chemistry of Fragrances" complied by D. H. Pybus and C. S. Sell, published by the Royal Society of Chemistry (Great Britain) 1999 ISBN 0854045287. Although somewhat arbitrary, the distinction between these three categories is based on a combination of volatility and perceived odor intensity. The present invention identifies a small group of predominantly top note fragrance ingredients which contrary to conventional wisdom and normal practice can be formulated into commercial quality fragrances which match and are preferred to current fragrances by typical consumers especially in the floral and fruity fragrance note areas which are widely used in personal core products. These fragrance compositions also improve some aspects of the problems outlined above. The fragrance ingredients have been chosen parameters. Fragrance compositions of the invention improve perfume performance in the following ways:

- the fragrance itself has a stronger impact in order that lower percentages of fragrance (10-25% of conventional fragrances) can be dosed into product formulations reducing the environmental load;
- the ingredients which comprise the fragrance are available from natural renewable resources e.g. from fermentation processes, or by simple procedures on materials available from vegetable matter;
- the ingredients are more readily biodegradable than those which comprise a more traditional fragrance composition;
- by working a small subset of fragrance ingredients it is possible to create attractive powerful fragrances which are hypoallergenic.

Thus it is an object of the present invention to provide high intensity, consumer acceptable fragrances, suitable for use in cosmetic, toiletry, personal care, personal cleansing product and adsorbent articles which are preferably hypoallergenic and can be formulated from fragrance materials available from sustainable natural sources and which have less environmental impact due to the lower dosage of carefully selected ingredient.

BRIEF SUMMARY OF THE INVENTION

The present invention encompasses the following embodiments.

(1) A high intensity fragrance composition for use in a cosmetic, toiletry, personal care, personal cleansing product or adsorbent article, which comprises by weight:

a) 75% to 100% of at least 2 fragrance ingredients where each fragrance ingredients

- consist of at least one kind of atoms selected from the group consisting of a carbon atom, a hydrogen atom, an oxygen atom and a nitrogen atom,
- comprise an ester functional group, an alcohol functional group or an aldehyde functional group;
- have boiling points between 100° C. and 300° C. at a pressure of 760 mm of mercury;
- have molecular weights within the range of 70 atomic mass units to 175 atomic mass units,
- have ClogP values between 0.00 and 4.00;

b) 0 to 25% of an essential oil; and c) 0 to 25% of a fragrance ingredient other than the fragrance ingredients in the above category a), wherein the sum of a), b) and c) equals 100%.

(2) The high intensity fragrance composition according to (1), in which the fragrance ingredients in category a) are selected from the group consisting of: allyl hexanoate, n-amyl acetate, isoamyl acetate, n-amyl propionate, anisic alcohol, anisic aldehyde, benzaldehyde, benzyl alcohol, benzyl acetate, butyl acetate, cinnamic alcohol, cinnamic aldehyde, citral, citronellol, coumarin, decalactone gamma, ethyl 2-methylbutyrate, ethyl butyrate, ethyl caproate, ethyl caprylate, ethyl heptanoate, ethyl lactate, ethyl propionate, eugenol, geraniol, heliotropine, trans-2-hexenal, cis-3-hexenol, cis-3-hexenyl acetate, cis-3-hexenyl propionate, hexyl acetate, isobutyl acetate, limonene, linalool, L-manthol, methyl benzoate, methyl salicylate, methyl anthranilate, octalactone gamma, 2-phenylethyl acetate, 2-phenylethylalcohol, 1-terpinen-4-ol, alpha-terpineol, vanillin, and 3-hydroxy-2-methyl-4-pyrone.

(3) The high intensity fragrance composition according to (1) or (2), in which 80 to 100% by weight of the high intensity fragrance composition are ingredients selected from the group consisting of: allyl hexanoate, anisic aldehyde, benzaldehyde, benzyl acetate, butyl acetate, isobutyl acetate, decalactone gamma, ethyl 2-methylbutyrate, ethyl butyrate, ethyl caproate, heliotropine, trans-2-hexenal, cis-3-hexenol, hexyl acetate, cis-3-hexenyl acetate, cis-3-hexenyl propionate, isoamyl acetate, n-amyl acetate, L-manthol, alpha-terpineol, 1-terpinen-4-ol, methyl benzoate, methyl anthranilate, 2-phenylethyl acetate, 2-phenylethylalcohol, vanillin and 3-hydroxy-2-methyl-4-pyrone.

(4) The high intensity fragrance composition according to any one of (1) to (3), in which 80 to 100% by weight of the high intensity fragrance composition are ingredients selected from the group consisting of: allyl hexanoate, anisic aldehyde, benzaldehyde, benzyl acetate, butyl acetate, isobutyl acetate, decalactone gamma, ethyl 2-methylbutyrate, ethyl butyrate, heliotropine, hexyl acetate, cis-3-hexenol, cis-3-hexenyl acetate, cis-3-hexenyl propionate, isoamyl acetate, n-amyl acetate, methyl benzoate, 2-phenylethyl acetate, 2-phenylethylalcohol and vanillin.

(5) The high intensity fragrance composition according to any one of (1) to (4), which comprises the fragrance ingredients in category a) comprising the alcohol functional group, in which 80% to 100% by weight of the fragrance ingredients in category a) comprising the alcohol functional group are ingredients selected from the group consisting of: cis-3-hexenol, L-menthol, 2-phenylethylalcohol, alpha-terpineol, 1-terpine-4-ol and 3-hydroxy-2-methyl-4-pyrone.

(6) The high intensity fragrance composition according to (5), in which 80% to 100% by weight of the fragrance ingredients in category a) comprising the alcohol functional group are selected from the group consisting of: cis-3-hexenol, 2-phenylethylalcohol, alpha-terpineol and 1-terpine-4-ol.

(7) The high intensity fragrance composition according to any one of (1) to (6), which comprises at least 4 fragrance ingredients in category a).

(8) The high intensity fragrance composition according to any one of (1) to (4), in which 50 to 100% by weight of the fragrance ingredients in category a) are ingredients selected from the group consisting of: anisic aldehyde, benzyl acetate, decalactone gamma, ethyl 2-methylbutyrate, ethyl butyrate, cis-3-hexenol, hexyl acetate, trans-2-hexenal, cis-3-hexenyl acetate, isoamyl acetate, 2-phenylethyl acetate, 2-phenylethylalcohol and vanillin.

(9) The high intensity fragrance composition according to (8), in which 50 to 100% by weight of the fragrance ingredients in category a) are ingredients selected from the group consisting of: anisic aldehyde, benzyl acetate, decalactone gamma, ethyl 2-methylbutyrate, ethyl butyrate, cis-3-hexenol, hexyl acetate, cis-3-hexenyl acetate, isoamyl acetate, 2-phenylethyl acetate, and 2-phenylethylalcohol.

(10) The high intensity fragrance composition according to any one of (1) to (9), in which 90 to 100% by weight of combined ingredients of the fragrance ingredients in category a) and fragrance ingredient in category c) have boiling points between 100° C. and 250° C. at a pressure of 760 mm of mercury.

(11) The high intensity fragrance composition according to any one of (1) to (10), which is hydroallergenic.

(12) The high intensity fragrance composition according to any one of (1) to (11), in which all of the ingredients are derived from natural sources.

(13) The high intensity fragrance composition according to any one of (1) to (12), which has a fruity or floral odor note.

(14) A product comprising the high intensity fragrance composition according to any one of (1) to (13), and water in an amount of at least 15% of the product, wherein the product is selected from the group consisting of a cosmetic, a toiletry, a personal care and a personal cleansing product.

(15) An adsorbent article comprising the high intensity fragrance composition according to any one of (1) to (13).

(16) A method for cleaning at lease one of a skin and a hair, which comprises applying an effective amount of a personal cleansing product comprising the high intensity fragrance composition according to any one of (1) to (13) to at least one of the skin and the hair with water.

According to one aspect of the invention, those fragrance compositions are used in cosmetic, toiletry, personal care products, personal cleansing products and absorbent articles for personal use.

According to a second aspect of the invention, the high intensity fragrance composition is preferably a hypoallergenic fragrance.

According to a further aspect of the invention, the high intensity fragrance composition preferably comprises between 50% and 100% of the materials derived from natural sources such as vegetable matter or from a fermentation process.

DETAILED DESCRIPTION OF THE INVENTION

All percentages herein are weight percentages unless specifically stated otherwise. All numerical values are taken to be approximately the given within the normal accuracy of measurement or calculation. All documents cited herein are incorporated by reference.

A fragrance composition as defined hereinafter is an essential part of the invention. A fragrance ingredient or perfume material, which terms are synonymous can be any compound used in a fragrance or perfume composition. A wide variety of odiferous materials are known for perfumery use, including materials possessing a variety of functional groups, such as alkenes, alcohols, aldehydes, ketones, esters, ethers, nitriles, amines, oximes, acetals, ketals, thiols, thioketones, imines, etc. Without wishing to be limited, in most cases, fragrance ingredients will have molecular weights between 70 atomic mass units and 400 atomic mass units to ensure sufficient volatility. Fragrance ingredients will not contain strongly ionizing functional groups such as sulphonates, sulphates, or quaternary ammonium ions. Fragrance ingredients are described more fully in S. Arctander, Perfume Flavors and Chemicals. Vols. I and II, Montclair, N.J., the Merck Index, $8^{th}$ Edition, Merck & Co., Inc. Rahway, N.J. and Allured's Flavor and Fragrance Materials 2008 Published by Allured Publishing Corp ISBN 1-932633-42-1 all are incorporated herein by reference.

In the following description, the components a), b) and c) of the invention fragrance composition will be identified as fragrance ingredients (category a)), optional essential oils (category b)) and other fragrance ingredients (category c)).

Fragrance Ingredients (Category a))

The ingredients of category a) of the invention are characterized by comprising fragrance ingredients which contain only atoms of carbon, hydrogen, oxygen and nitrogen. They are further characterized by: specific chemical functional groups, having molecular weight within a range of 70 atomic mass units to 175 atomic mass units, having boiling points at standard pressure of about 760 mm of mercury within the range of 100° C. to 300° C. and having calculated partition coefficient (Clog) values between 0.00 and 4.00.

Functional Groups

The empirical testing of the intensity of fragrance ingredients yielded a higher proportion of alcohols, esters and aldehydes as high intensity fragrance ingredients than are typically present in commercial fragrance formulations. Alcohol, ester and aldehyde functional groups have their common meaning in chemistry and their structure and properties are set out in many text books such as "Organic Chemistry" by Clayden, Greeves, Warren and Wothers Oxford University Press 2001. In this specification esters are formally derived from the reaction of carboxylic acid and any of alcohol, phenol, hetero-arenol or enol with the elimination of water. Alkyl derivatives of other acidic compounds e.g. sulphate or sulphonate esters, or phosphate esters, ortho esters, carbonates (urethanes), and cyanates are not considered to be esters within this definition.

Aldehydes are functional groups in which a carbonyl group is bound to a hydrogen atom and an alkyl, cycloalkyl, alkenyl or aryl group.

Alcohols are compounds in which the hydroxyl group is attached to a saturated, unsaturated or aromatic carbon atom as part of an alkyl, alkenyl or aryl group. Alcohols include primary secondary and tertiary alcohols of alkyl, alkenyl or alicyclic groups, also including compounds having a stable enol tautomeric from such as Veltol™ (3-hydroxy-2-menthl-4-pyrone CAS 118-71-8), or phenolic compounds such as eugenol. Thiols are not considered alcohols in this specification.

A preferred group of alcohols which are particularly useful as high intensity fragrance ingredients is the group consisting of cis-3-hexen-1-ol, 2-phenylethanol, L-menthol, alpha terpineol, 1-terpinen-4-ol and Veltol™. When alcohols are present in the invention composition, preferably 80% to 100% of the alcohols are selected among the six above mentioned alcohols.

A more preferred group of alcohols which is useful as high intensity fragrance ingredients is the group consisting cis-3-hexen-1-ol, 2-phenylethanol, alpha terpineol and 1-terpinen-4-ol Many fragrance ingredients possess more than one functional group; however compounds which contain alcohol, ester or aldehyde functionalities are so classified irrespective of other functional groups present.

Molecular Weight Range

Ingredients suitable for use in high intensity fragrance compositions will predominantly comprises esters, aldehydes and alcohols having molecular weights equal to or less than 175 atomic mass units (amu), preferably equal to or less than 165 amu and more preferably equal to or less than 155 amu to be sufficiently volatiled to be readily perceived. Furthermore the perfume compounds will have molecular weights equal to or greater than 70 amu, preferably equal to or greater than 80 amu and even more preferably equal to or greater than 90 amu. Lower mass ingredients may be too water soluble to function as perfumes.

ClogP

ClogP refers to the octanol/water partitioning coefficient (P) of fragrance ingredients. The octanol/water partitioning coefficient of fragrance ingredient is the ratio between its equilibrium concentrations in octanol and in water. The partitioning coefficients of fragrance ingredients are more conveniently given in the form of their logarithm to the base 10, logP. The logP of many fragrance ingredients have been reported; for example, the Pomona92 database, available from Daylight Chemical Information Systems, Inc. (Daylight CIS), Irvine, Calif., contains many, along with citations to the original literature. ClogP values can be calculated using the fragment approach as described in "Partition Coefficients and Their Uses" by A Leo, C Hansch and D Elkins in Chem. Rev. vol 71 (6) pages 525-616 (1971). However, the ClogP values reported herein are most conveniently calculated by the "CLOGP" program available within the Chemoffice Ultra Software version 9 available from CambridgeSoft Corporation, 100 CambridgePark Drive, Cambridge, Mass. 02140 USA or CambridgeSoft Corporation, 8 Signet Court, Swamis Road, Cambridge CB5 8LA UK. The ClogP values are preferable used instead of the experimental logP values in the selection of fragrance ingredient which are useful in the present invention.

In order for high intensity fragrances to be effective they need to be noticeable in a range of bases which include solid products predominantly aqueous products perhaps containing some emulsified oil or surfactant, oil based products and products which contain water emulsified in oil. Fragrance ingredients may have ClogP values between 0.00 and 4.00, preferably these values are between 0.50 and 3.50 and more preferably between 1.00 and 3.00 and especially a high intensity fragrance composition has ClogP values within the range between 1.00 and 3.00; it is more preferable if between 70% and 100% by weight of a high intensity fragrance composition has ClogP values within the range between 1.00 and 3.00 and it is even more preferable if between 90% and 100% by weight of a high intensity fragrance composition has ClogP values within the range between 1.00 and 3.00.

Boiling Point

The boiling points of many fragrance ingredients, at standard pressure of 1 atmosphere (760 mmHg), are given in e.g., "Perfume and Flavor Chemicals (Aroma Chemicals)", Steffen Arctander, as mentioned hereinbefore. Boiling points of many fragrance ingredients can be found in the following sources: Properties of Organic Compounds Database CD-ROM Ver. 5.0 CRC Press Boca Raton, Fla. Flavor and Fragrance 1995 Aldrich Chemical Co. Milwaukee, Wis. STN database/on-line Design Institute of for Physical Property Date American Institute of Chemical Engineers STN line/on-line Beilstein Handbook of Organic Chemistry Beilstein Information Systems. When unreported, boiling points of perfume ingredients can also be estimated. The method of Stein and Brown (J. Chem. Inf. Sci. vol 34 p 581-587 (1994)) can be used to estimate the boiling points of organic compounds. A review of this and alternative methods in given in chapter 2 of "Handbook of Property Estimation Methods for Chemicals Environmental and Health Sciences by R S Boethling and D McKay Published by CRC Press 2000 ISBN 1566704561. The following computer program is also useful for estimating boiling points following the method of Stein and Brown MPBPWIN (copyright United States Environmental Protection Agency version 1.42) which is part of the package EPI suite (copyright United State Environmental Protection Agency version 3.20) referenced previously. Since measured boiling points may not always be available and there may well be discrepancies between measured values, the calculation method of Stein and Brown provides a standard method to determine a boiling points for the purposes of this specification.

Fragrance ingredients for high intensity fragrance compositions have boiling points between 100° C. and 300° C., preferably they have boiling points between 100° C. and 275° C. and more preferably between 100° C. and 250° C. It is also preferable if the fragrance ingredients described hereinafter as category c) materials have boiling points equal to or below 300° C. Indeed it is preferred if at least 80% by weight of the ingredients within the fragrance composition of the invention have boiling points equal to or below 300° C. it is more preferred if 90% by weight of the ingredients within the fragrance composition of the invention have boiling points below 300° C. It is even more preferred if at least 80% by weight of the ingredients within the fragrance composition of the invention have boiling points equal to or below 275° C. and it is yet more preferred if 90% by weight of the ingredients within the fragrance composition of the invention have boiling points below 275° C.

Hypoallergenic Property

Preferably the high intensity fragrance composition is a hypoallergenic fragrance composition. A hypoallergenic fragrance composition is one that has a reduced potency for allergic reaction. Materials which are known to be strong allergens from prior art publications (See for example Contact Dermatitis vol. 50, pp 65-76 (2004) and ibid vol. 49, pp 236-240 (2003)) are often used directly as ingredients in fragrance compositions or they may be present as impurities in other ingredients or as components in essential oils. Those fragrance ingredients specified as allergenic substances within the $7^{th}$ amendment of the Cosmetic Directive, Directive 2003/15/EC ($7^{th}$ amendment to Directive 76/768/EEC) which are amyl cinnamic aldehyde (122-40-7), amyl cinnamic alcohol (101-85-9), anisyl alcohol (105-13-5), benzyl alcohol (100-51-6), benzyl benzoate (120-51-4), benzyl cinnamate (103-41-3), benzyl salicylate (118-58-1), cinnamic aldehyde (104-55-2), cinnamyl alcohol (104-54-1), citronellol (106-22-9), coumarin (91-64-5), eugenol (97-53-0), farnesol (4602-84-0), geraniol (106-24-1), hexyl cinnamic aldehyde (101-86-0), hydroxycitronellal (107-95-5), 4-(4-hydroxy-4-methylpentyl)cyclohex-3-ene-1-carbaldehyde (31906-04-4), isoeugenol (97-54-1), Lilial (80-54-6), limonene (5989-27-5), linalool (78-70-6), methyl heptine carbonate (111-12-6) and 3-methyl-4-(2,6,6-trimethyl-1-cyclohex-2-enyl)but-3-en-2-one (127-51-5), citral (5392-54-6), Oakmoss extract (90028-68-5) and treemoss extract (90028-67-4), are preferably each restricted to below 1,000 ppm (weight/weight) and even more preferably to below 100 ppm (weight/weight) irrespective of their source.

Most preferably, the following fragrance ingredients: isoeugenol (97-54-1), cinnamic aldehyde (104-55-2), cinnamic alcohol (104-54-1), Amyl cinnamic aldehyde (122-40-7), citral (5392-40-5), eugenol (97-53-0), farnesol (4602-85-0), lilial (80-54-6) and coumarin (91-64-5), should not be intentionally added to fragrance compositions of the current application due to evidence that they are known to be strong allergens.

Biodegradability and Naturally Sourced Materials

It is also preferred if the high intensity fragrances of the invention are comprised of ingredients which are biodegradable. Fragrance ingredients are deemed biodegradable if they are classified as readily biodegradable by the Organization for Economic C0-operation and Development (OECD) biodegradability tests, especially tests 301C, 301D, 301F and 310.

Certain biodegradability date is publicly available, for example, The Flavor and Fragrance High production Volume (HPV) Consortia of Washington D.C., USA has a submitted a document annotated 20115461B to the Environmental Protection Agency in 2004 as "The Robust Summary" from The Terpene Consortium. Citronellol (OECD 301F), Geraniol (OECD 301B) and Citral (OECD 301B) are all reported as readily biodegradable.

Similarly The Flavor and Fragrance HPV (High Production Volume) Consortia of Washington D.C., USA has submitted a document annotated AR201-1345A to the EPA in 2002 as "The Test Plan for Benzyl Derivatives" from The Aromatic Consortium. Benzyaldehyde, methyl benzoate and benzyl acetate are all reported as readily biodegradable following methods OECD 301B or OECD 301F.

As published date is most often linked to high production volume fragrance materials, certain publicly available software can be used as guide to likely biodegradability for a wider range of fragrance materials One indicator of biodegradability for w wide range of fragrance materials can be obtained by using the program BioWIN, version 4.50 of which forms part of the EPI suite (copyright United States Environmental Protection Agency) group of programs version 3.20 of which is freely available from the United States Environmental Protection Agency.

It is preferred if the fragrance compositions of the invention are derived from natural sources i.e. the raw materials are of vegetable or microbiological origin including products derived from this material by enzymatic processes or by traditional processes of preparation e.g. drying, torrefaction or fermentation as defined by international standard ISO-9235 "Aromatic Natural Materials—Vocabulary".

Without wishing to be limited in any way table 1, below, lists examples of naturally available, mostly readily biodegradable esters, alcohols and aldehydes, suitable for use as fragrance ingredients in the high intensity fragrance compositions of the invention. Where available measured values for the octanol water partition coefficients and boiling point are included along with estimated values. A hyphen indicates an unreported value while the term Med in the column readily biodegradable refers to a compound which biodegrades but more slowly than those designated as readily biodegradable.

TABLE 1

| Ingredient Name | CAS # | Mol wt | ClogP | LogP | Estimated boiling point | Measured Boiling Point | Readily biodegradable |
|---|---|---|---|---|---|---|---|
| ALLYL HEXANOATE | 123-68-2 | 156 | 3.07 | — | 189 | 186 | Yes |
| n-AMYL ACETATE | 628-63-7 | 130 | 2.30 | 2.30 | 148 | 149 | Yes |
| ISOAMYL ACETATE | 123-92-2 | 130 | 2.17 | 2.25 | 135 | 142 | Yes |
| n-AMYL PROPIONATE | 624-54-4 | 144 | 2.70 | 2.66 | 170 | 169 | Yes |
| ANISIC ALCOHOL | 105-13-5 | 138 | 1.02 | 1.10 | 244 | 259 | Yes |

TABLE 1-continued

| Ingredient Name | CAS # | Mol wt | ClogP | LogP | Estimated boiling point | Measured Boiling Point | Readily biodegradable |
|---|---|---|---|---|---|---|---|
| ANISIC ALDEHYDE | 123-11-5 | 136 | 1.78 | 1.76 | 222 | 248 | Yes |
| BENZALDEHYDE | 100-52-7 | 106 | 1.49 | 1.48 | 181 | 179 | Yes |
| BENZYL ALCOHOL | 10-51-6 | 108 | 1.10 | 1.10 | 206 | 205 | Yes |
| BENZYL ACETATE | 140-11-4 | 150 | 1.96 | 1.91 | 216 | 213 | Yes |
| BUTYL ACETATE | 123-84-4 | 116 | 1.77 | 1.78 | 126 | 126 | Yes |
| CINNAMIC ALCOHOL | 104-54-1 | 134 | 1.61 | 1.95 | 249 | 250 | Yes |
| CINNAMIC ALDEHYDE | 104-55-2 | 132 | 2.05 | 1.90 | 227 | 246 | Yes |
| CITRAL | 5392-40-5 | 152 | 2.95 | — | 217 | 229 | Yes |
| CITRONELLOL | 106-22-9 | 156 | 3.25 | 3.91 | 228 | 224 | Yes |
| COUMRIN | 91-64-5 | 146 | 1.41 | 1.39 | 291 | 302 | Yes |
| DECALACTONE GAMMA | 706-14-9 | 170 | 2.36 | 2.72 | 282 | — | Yes |
| Ethyl 2-METHYL BUTYRATE | 7452-79-1 | 130 | 2.08 | — | 135 | 131 | — |
| ETHYL BUTYRATE | 105-54-4 | 116 | 1.77 | 1.73 | 126 | 121 | Yes |
| ETHYL CAPROATE | 123-66-0 | 144 | 2.83 | — | 170 | 167 | Yes |
| ETHYL CAPRYLATE | 106-32-1 | 172 | 3.88 | — | 211 | 208 | Yes |
| ETHYL HEPTANOTE | 106-30-9 | 158 | 3/36 | — | 191 | 187 | Yes |
| ETHYL LACTATE | 97-64-3 | 118 | 0.33 | −0.18 | 166 | 154 | Yes |
| ETHYL PROPIONATE | 105-37-3 | 102 | 1.24 | 1.21 | 102 | 99 | Yes |
| EUGENOL | 97-53-0 | 164 | 2.40 | 2.27 | 264 | 253 | No |
| GREANIOL | 106-24-1 | 154 | 2.97 | 3.56 | 240 | 230 | Yes |
| HELIOTROPINE | 120-57-0 | 150 | 1.76 | 1.05 | 257 | 263 | Yes |
| TRANS-2-HEXENAL | 6728-26-3 | 98 | 1.58 | — | 139 | 146 | Yes |
| CIS-3-HEXENOL | 928-96-1 | 100 | 1.40 | — | 166 | 156 | Yes |
| CIS-3-HEXENYL ACETATE | 3681-71-8 | 142 | 2.34 | 2.34 | 177 | — | Yes |
| CIS-3-HEXENYL PROPIONATE | 33467-74-2 | 156 | 2.87 | — | 197 | — | Yes |
| HEXYL ACETATE | 142-92-7 | 144 | 2.83 | 2.79 | 170 | 171 | Yes |
| Iso-BUTYL ACETATE | 110-19-0 | 116 | 1.64 | 1.78 | 112 | 116 | Yes |
| LIMONENE | 5989-27-5 | 136 | 4.35 | 4.57 | 176 | 176 | No |
| LINALOOL | 78-70-6 | 154 | 2.75 | 2.97 | 204 | 197 | No |
| L-MENTHOL | 2216-51-5 | 156 | 3.23 | 3.23 | 219 | 216 | No |
| METHYL BENZOATE | 93-58-3 | 136 | 2.11 | 2.12 | 196 | 199 | Yes |
| METHYL SALICYLATE | 119-36-8 | 152 | 2.33 | 2.55 | 252 | 223 | Yes |
| METHYL ANTHRANILATE | 134-20-3 | 151 | 2.12 | 1.88 | 264 | 256 | Med |
| OCTALACTONE, GAMMA | 104-50-7 | 142 | 1.30 | — | 248 | — | Yes |
| PHENYLETHYL ACETATE | 103-45-7 | 164 | 2.28 | 2.30 | 234 | 233 | Yes |
| PHENYLETHYL ALCOHOL | 60-12-8 | 122 | 1.33 | 1.36 | 225 | 218 | Yes |
| 1-TERPINEN-4-OL | 562-74-3 | 154 | 2.75 | 3.26 | 212 | 209 | No |
| TERPINEOL, ALPHA | 98-55-5 | 154 | 2.63 | 2.98/3.23 | 214 | 220 | No |
| VANILLIN | 121-33-5 | 152 | 1.28 | 1.21 | 274 | 285 | Yes |
| VELTOL ™ | 118-71-8 | 126 | 0.10 | 0.09 | 267 | — | Yes |

In a high intensity fragrance composition it is preferred if the fragrance composition comprises at least 75% by weight, preferably at least 80% by weight, more preferably at least 85% by weight, especially preferably at least 90% by weight and even more especially preferable that 100% by weight of the category a) fragrance ingredients. It is especially preferred if the high intensity fragrance ingredients come from those listed in table 1.

A preferred group of high intensity fragrance ingredients i.e. category a) materials includes: allyl hexanoate, anisic aldehyde, benzaldehyde, benzyl acetate, butyl acetate, isobuthyl acetate, decalactone gamma, ethyl 2-methylbutyrate, ethyl butyrate, ethyl caproate, heliotropine, trans-2-hexenal, cis-3-hexenol, hexyl acetate, cis-3-hexenyl acetate, cis-3-hexenyl propionate, isoamyl acetate, n-amyl acetate, L-menthol, alpha-terpineol, 1-terpinen-4-ol, methyl benzoate, methyl anthranilate, 2-phenylethyl acetate, 2-phenylethyl alcohol, vanillin and Veltol™. It is preferred if 80-100% and even more preferred if 90-100% of the high intensity fragrance composition is selected from these ingredients.

A further preferred group of the fragrance ingredients of category a) materials includes: allyl hexanoate, anisic aldehyde, benzaldehyde, benzyl acetate, butyl acetate, isobuthyl acetate, decalactone gamma, ethyl 2-methylbutyrate, ethyl butyrate, heliotropine, hexyl acetate, cis-3-hexenol, cis-3-hexenyl acetate, cis-3-hexenyl propionate, isoamyl acetate, n-amyl acetate, methyl benzoate, 2-phenylethyl acetate, 2-phenylethyl alcohol and vanillin. It is also preferred if 80-100% and even more preferred if 90-100% of the high intensity fragrance composition is selected from these ingredient.

Preferably, in the high intensity fragrance composition of the invention, 50-100% of the fragrance ingredients of category a) are selected from the following ingredients anisic aldehyde, benzyl acetate, decalactone gamma, ethyl 2-methylbutyrate, ethyl butyrate, cis-3-hexenol, hexyl acetate, trans-2-hexenal, cis-3-hexenyl acetate, isoamyl acetate, 2-phenylethyl acetate, 2-phenylethyl alcohol and vanillin.

According to a further embodiment, 50-100% of the fragrance ingredients of category a) are selected from the following ingredients: anisic aldehyde, benzyl acetate, decalactone gamma, ethyl 2-methylbutyrate, ethyl butyrate, cis-3-hexenol, hexyl acetate, cis-3-hexenyl acetate, isoamyl acetate, 2-phenylethyl acetate, 2-phenylethyl alcohol.

Fragrances for consumer products are usually complex, comprising a large number of fragrance ingredients to perform satisfactorily. Typically commercial fragrance may contain from 20 to 200 individual ingredients. While it is known to use a single material as a product's fragrance the result is usually inferior to a fully formulated fragrance. As the number of fragrance ingredients increases so does the creative scope. It has been found that consumer desirable fragrances can be formulated from groups of 2 to 10 ingredients. So for fragrance quality at least two high intensity fragrance ingredients, preferably more than 3 ingredients and especially preferably more than 5 ingredients. There is no distinct upper limit; however the increase in creative scope on increasing from 2 to 4 ingredients is much greater than in going from 20 to 22 ingredients. Commercially successful fragrances can be created from as few as two well characterized fragrance ingredients and a range of attractive successful fragrance having different fragrance notes can be created from at least 4, preferably from 4 to 12 high intensity fragrance ingredients.

Optional Essential Oils (Category b))

Compositions of the present invention may optionally contain up to 25% by weight of essential oils. Essential oils are produced by subjecting suitable natural materials such as plant components: leaves, flowers, seeds, roots or stems to an extraction process. The extraction processes are well known to those skilled in the art and are described in The Essential Oils by E Guenther published in 1949 by D van Nostrand. Essential oils can undergo additional processes to rectify and purify the oils for example by removing the terpene components via a "head cut" and/or removing the wax components via a "tail cut". A preferred group of essential oils for the present invention is a group consisting of Amyris oil, cedarwood oil, copaiba balsam, menthe oil pays, myrrh resin, patchouli oil, sandalwood, vanilla (absolute) and vetiver oil. While it is known to formulate fragrances entirely from essential oils thereby having a natural fragrance this is not really practical for consumer products; the raw materials are often too expensive and not available in the quantities necessary for high volume consumer products. Thus the proportion of essential oil in any high intensity fragrance should be at most 25% by weight, more preferably at most 15% by weight and more preferably at most 5% by weight.

Other Fragrance Ingredients (Category c))

The high intensity fragrance composition of the invention comprises c) 0 to 25% of a fragrance ingredient other than the fragrance ingredients in category a).

The fragrance ingredients of category c) may be selected among any ingredients conventionally used as fragrance ingredients but are different from the ingredients of category a), i.e. they may have other functional groups than ester, alcohol or aldehyde functions, which may but need not meet the criteria for a fragrance ingredient of category a), or they may be compounds containing ester, alcohol or aldehyde functional groups which have molecular weight, boiling points or ClogP values outside the ranges defined as category a) materials. Without wishing to be limited, examples of category c) materials include α-ionone (CAS 127-41-3), α-sinensal (CAS 17909-77-2), β-caryophylene (CAS 87-44-5), D-carvone (CAS 2244-26-8), 1,8-cineole (CAS 470-82-6), citronellyl nitrile (CAS 41455-62-2), Cyclacet® International Flavors and Fragrances Corp. (CAS 5413-60-5), δ-damascone (CAS 23726-92-3), Dihydromyrcenol (CAS 18479-58-8), Ethylene brassylate (CAS 105-95-3), indole (CAS 120-72-9), Methyl dihydrojasmonate (CAS 24851-98-7), Nerolidol (CAS 7212-44-4).

Preferably, the fragrance ingredients of category c) have also a molecular weight between 70 amu and 175 amu.

More preferably, 90% to 100% by weight of the combined ingredients of the fragrance ingredients in category a) and fragrance ingredient in category c) are classified as readily biodegradable by the tests described hereinabove.

More preferably, 90% to 100% by weight of the combined ingredients of the fragrance ingredients in category a) and fragrance ingredient in category c) have boiling points between 100° C. and 250° C. at a pressure of 760 mm of mercury.

Most preferably, all of the fragrance ingredients of the high intensity fragrance composition are derived from natural sources.

Exclusions and Limitations

1. Musks

Among the perfumery materials which are known to have undesirable characteristics and are therefore preferably excluded from the invention perfume compositions are nitro musks as exemplified by musk ketone (CAS 81-14-1), molecules which persist in the environment such as polycyclic musks as exemplified by 1,3,4,6,7,8-hexahydro-4,6,6,7,8,8-hexamethylcyclopenta-gamma-2-benzopyran (CAS 1222-05-5) and 1-(5,6,7,8-tetrahydeo-3,5,5,6,8,8-hexamethyl-2-naphtalenyl)-ethan-1-one (CAS 1505-02-1).

2. Essential Oils

While the proportion of essential oils is limited to 25% of the total fragrance composition, if the fragrance is hypoallergenic, any essential oil containing the herein above mentioned allergenic substances must only be used at such levels as not to exceed the limits set for an hypoallergenic fragrance within this specification.

3. Solvents

Solvents are defined as relatively low odor liquids which can dissolve a target material in reasonable proportions. For perfumery use solvents may be defined as liquids having sufficiently little odor that they can be added at 30% by weight to a fragrance composition without substantially changing the odor of that composition. Solvents are used in the fragrance industry to dilute olfactively powerful ingredients and to facilitate the handing of solid ingredients by dissolving them and handing them as liquids. It is preferable to avoid diluting high intensity fragrance compositions if possible. Solid ingredients should preferably be dissolved in other fragrance composition rather than in a solvent. However sometimes e.g. for ease of manufacture, it may be necessary to add a solvent to a high intensity fragrance. If solvents have to be used they should preferably be naturally derived materials selected from among:

- long chain mono- di or triglyceride esters, which may include low odor natural oils which fit the definition of solvents such as sunflower oil rapeseed oil, canola oil, almond oil, jojoba oil or monoglycerides such as glycerol monoleate,
- simple esters of long alkyl chain carboxylic acids such as those from coconut oil, soy oil, repeseed oil or sunflower oil having following formula (I):

$$R^2COOR^3 \qquad (I)$$

wherein $R^2$ can be single $C_8$-$C_{20}$ alkyl chains e.g. undecyl or a mixture of $C_8$-$C_{20}$ alkyl or alkenyl chains and $R^3$ is methyl, ethyl, n-propyl, isopropyl, n-butyl or isobutyl group. These esters may include fractionated oils as well as the complete oil.

Solvents may also include methyl or ethyl esters of $C_2$ to $C_{12}$ substituted naturally derived fatty acids, such as lactic acid, tartaric acid, citric acid, gluconic acid, succinic acid, adipic acid, sebacic acid and azelaic acid.

Solvents may also be glycols such as 1,2-propylene glycol or 1,3-propylene glycol or dipropylene glycol or 1,2-buthlene glycol or 1,3-butylene glycol or 2,3-butylene glycol and acetyl or propionyl esters of glycols such as triacetin.

Solvents may also include alcohols such as ethanol and mixtures of any of above in any proportions.

Preferably the solvents should be from naturally derived sources.

Solvents which should not be used in high intensity fragrance compositions of the invention include the carbitol ethers defined as $R—(OCH_2CH_2)_n—OR^1$ where n=1, 2, or 3 and R=($C_1$ to $C_7$) alkyl or phenyl or alkyl substituted phenyl and R1 is H or ($C_1$ to $C_7$) alkyl or phenyl or alkyl substituted phenyl and the phthalate esters especially the phthalate esters of low molecular weight alcohols such as dimethyl phthalate, diethyl phthalate, dibutyl phthalate.

In the specification solvents are excluded from the calculation of percentages of ingredients within a fragrance composition.

High intensity fragrance compositions of the invention are found to provide equal or stronger fragrance odor intensity compared with a conventional fragrance of similar fragrance note at a minimum of a four fold greater dilution in a sensory test dosed at normal dosage in a product, using the protocol of a forced choice triangle difference test. A description of triangle difference tests can be found in "Sensory Evaluation Techniques 3$^{rd}$ Edn." by M C Meilgaard G V Civille and B T Carr Published by CRC Press in 1999, ISBN 0849302765. A procedure for performing a forced choice triangle test is also available as ISO 4120 (20 Oct. 2007) "Sensory Analysis Methodology".

Fragrance Dosing Level

Fragrance dosage depends on the type of product and some typical dosage levels are shown in table 2 below. High intensity fragrances are dosed at lower levels than in conventionally formulated fragrances typically by a factor of 4 times to 10 times less. Typically hydroallergenic high intensity fragrances will be dosed below 0.3% by weight of the final formulation, preferably below 0.2% by weight of the final formulation, more preferably below 0.1% by weight of the final formulation and particularly preferably below 0.05% by weight of the final formulation.

Products

Products to be fragranced according to the invention are cosmetic, toiletry, personal care, personal cleansing products and adsorbent articles which are not intended for human or animal ingestion and especially those products which are to be described as skin mild or for sensitive skin or which will remain on or in close proximity to the skin. Included within the definition of products to be ingested for purposes of the present invention are products for dental and oral care, such as toothpastes, mouth washes and lip balms which although not intended for ingestion may nevertheless accidentally enter the gastrointestinal tract.

Cosmetic, toiletry and personal care products may be considered as leave on products insofar as they are not removed alter application, whereas personal cleansing products are rinsed off the skin after application.

Cosmetic toiletry and personal care compositions include powders, creams, emulsions, lotions gels and oils for the skin (face, hands feet etc) tinted bases (liquids and pastes) and liquid impregnated tissues; products for applying and removing make-up from the face and eyes; hair care products including: hair tints and bleaches, products for waving, straightening, setting and fixing hair; shaving products including: creams, foams mousses and depilatory products; sun bathing products and products for tanning without the sun; deodorant and antiperspirant products including sticks, liquid roll-on applicators and pressurized sprays.

Personal cleansing products for the skin include toilet soaps, deodorant soaps, bath and shower preparations (salts, foams, lotions, liquids oils, gels etc.) and moist wipes. Hair cleansing products include shampoos and conditioners.

Many of the products will contain a certain proportion of water and such products will usually contain some surface active material, either as an emulsifier, if the product is an emulsion, or a detergent active material if the product has some kind of cleaning function. For cleaning products the concentration of surface active material in the product will be within the range 0.1-60% by weight; usually the level of surface active material will be 50% by weight or lower; for most products the level of surface active material will be 30 by weight or lower. One the other hand, the level of surface active material will usually be at least 0.1% by weight preferably greater than 1.0% and more preferably greater than 3.0% by weight. For products which have a cleaning function it is likely the level of surface active material will be higher, typically greater than 10% by weight and preferably greater than 15% by weight.

Examples of leave-on products containing emulsifiers are: hand and body lotions. Make up removing lotions, skin creams, sunscreen products and sunless tanning products, body freshener and hair sprays. Also included are articles of manufacture impregnated with liquids, for example pads or wipes impregnated with lotions for make up application or removal, or to apply sunscreen compounds or sunless tanning agents, for personal cleansing e.g. as moist toilet tissue or body wipes. Examples of cleansing products containing detergents are: shampoos, body washes, liquid soaps. Articles or substrates such as pads, sponges or wipes made from non woven textiles, may be impregnated with high intensity fragrances alone or as part of a mixture. Some cleaning products may be considered leave on products even though they are used for cleansing if there is no rinsing or further cleaning action after use. Baby wipes are an example, although used for cleaning the liquid deposited on the skin is not removed by rinsing.

Typical quantities of water, surface active material and both conventional and high intensity fragrance listed as weight percentages, dosed in different kinds of product are set out in table 2 below.

TABLE 2

| Product | Surfactant % | Water % | Conventional Perfume % | High Intensity Perfume % of the invention |
|---|---|---|---|---|
| Oil in water skin cream | 10 | 60 | 0.2 | 0.05 |
| Water-in-oil skin cream | 2 | 60 | 0.4 | 0.1 |
| Eye make-up remover | 5 | 60 | 0.2 | 0.05 |
| Shampoo | 20 | 75 | 0.5 | 0.1 |
| Hair conditioner | 5 | 90 | 0.5 | 0.1 |
| Cleansing Wipes* | 5 | 90 | 0.2 | 0.02 |
| Lotion skin Wipes* | 5 | 80 | 0.1 | 0.02 |
| Body Wash | 15 | 80 | 1.0 | 0.2 |
| Toilet Soap | 60 | 35 | 1.0 | 0.2 |

*figures based on composition of liquid used to impregnate the wipe.

The formulation and manufacture of cosmetic, toiletry, personal care and personal cleansing products in which high intensity fragrance compositions of the invention may be used are well known to those skilled in the art; reference may be made to the following words which are incorporated herein by reference:

Formulating Detergents and Personal Care Products A guide to Products Development by L Ho Tan Tai, ISBN 1-893997-10-3 published by the AOCS Press, and to Harry's Cosmeticology published by CHS Press $8^{th}$ Edn. 2000 ISBN 0820603724, as well we to the following patents or patent applications:

Shampoos and Hair Conditioners:

U.S. Pat. Nos. 6,162,423; 5,968,286; 5,935,561; 5,932,203; 5,837,661; 5,776,443; 5,756,436; 5,661,118; 5,618,523.

Liquid Soap and Skin Washing Products:

U.S. Pat. No. 3,697,644; U.S. Pat. No. 4,065,398; U.S. Pat. No. 4,387,040.

Moist Wipes:

U.S. Pat. No. 4,775,582; WO200207701; WO2007069214; WO9516474.

All of these patents are incorporate herein by reference.

The Surfactant Systems

The patent invention, especially in the aspect relating to personal cleansing compositions that are normally rinsed after application, like shampoos, liquid soaps and bath or shower products, comprises from about 0.1% by weight to about 60% by weight, preferably from about 3% by weight to about 50% by weight, more preferably from about 3% by weight to about 30% by weight, even more preferably from about 5% by weight to about 22% by weight of a surfactant system. This surfactant system comprises anionic, nonionic, cationic, and/or zwitterionic type surfactants or mixtures thereof. For non-shampoo surfactant systems the surfactant system typically comprises at least one surfactant selected from the group consisting of soap, acylglutamates, alkyl sarcosinates, alkylpolyethyleneglycol sulphates, alkylglyceryl ether sulphonates, and/or acyl isethionates.

Emulsifiers

The non-rinsed cosmetic, toiletry and personal care compositions described herein can contain various emulsifiers which are useful for emulsifying the various components of the products. Suitable emulsifiers can include any of a wide variety of nonionic, cationic, anionic, and zwitterionic surface active materials as disclosed in publications such as McCutcheon's, Detergents and Emulsifiers, North American Edition (1986), published by Allured Publishing Corporation and in the following US patents: U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al, issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% by weight to about 25% by weight, more preferably from about 1% by weight to about 10% weight of the product composition.

Whenever possible the surfactants and emulsifiers are preferably naturally derived, and readily biodegradable.

Additional Optional Components for Leave-on Personal Care Products

A variety of additional components can be incorporated into the non-rinsed compositions which may be preserved according to the invention. Non-limiting examples of there additional components include vitamins and derivatives thereof (e.g., ascorbic acid, vitamin E, tocopheryl acetate, retonic acid, retinol retinoids, and the like); thickening agents such as cross linked polyacrylate polymer; suspending agents such as ethylene glycol distearate and the like; preservatives for maintaining the antimicrobial integrity of the compositions; skin penetration aids such as dimethylsulfoxide (DMSO) 1-dodecylazacycloheptan-2-one (available as Azon from the Upjohn Co.) and the like; skin sensates, astringents, skin soothing agents, skin healing agents and the like, non-limiting examples of there aesthetic components include panthenol and derivatives (e.g. ethyl panthenol), pantathenic acid and its derivatives witch hazel distillate, allantoin, bisabalol, dipotassium glycyrrhizinate and the like. Other useful actives include skin bleaching (or lightening) agents including but not limited to hydroquinone, ascorbic acid, kojic acid and sodium metabisulfite. Actives which are especially useful for hair care compositions include anti-dandruff actives such as zinc pyrithione, octopirox, selenium disulfide, sulfur, coal tar, and the like, and hair curling and/or straightening actives as are well known in the art.

Additional Optional Components for Personal Cleansing Compositions

A wide variety of additional components can be employed in the hair care and skin cleaning compositions which may be preserved according to the current invention. Non-limiting examples include the following: sunscreening agents, sunless tanning agents, conditioning agents, humectants and moisturizers, carboxylic acid copolymer thickeners and emollients.

Water

Some of the cosmetic, toiletry, personal care, personal cleansing product and adsorbent articles into which fragrances of the invention can be incorporated may only contain a small percentage of water by weight, but liquid, gel, and paste products will usually contain significant proportions of water as indicated in table 2, because of its safety, environmental compatibility and low cost. Typically such products comprise from about 15% by weight to about 99% by weight, preferably from about 25% by weight to about 99% by weight, of water. For personal care and personal cleansing products containing at least 30% water it is preferred if the products have pH values between 5.0 and 8.0 at 25° C.

Method of Use for Personal Cleansing Products.

The present compositions are used in a conventional manner for cleaning the skin and/or hair and to provide olfactory aesthetic benefit. An effective amount of the product, typically from about 1 g to about 15 g the composition, is applied to the body or hair that has preferably been wetted, generally with water. Application includes dispensing of the composition onto the hand, onto the body or hair, or onto a washing implement, e.g., wash cloth, sponge, etc., and typically includes working the composition with the hands to develop lather. The lather can stand on the body for a length of time or can be rinsed immediately with water. Once the product is rinsed from the body the washing procedure can be repeated.

Adsorbent Articles

High intensity fragrance composition may be advantageously used in disposable adsorbent articles which are placed against the skin to contain or adsorb discharges or exudates from the body. Examples of disposable absorbent articles include disposable nappies for babies and training pants for older infants; feminine hygiene products such as sanitary towels, panti-liners and tampons; and incontinence briefs. Such products generally contain an adsorbent material such as spun wool, cotton, cellulosic fibers, synthetic textile fibers as well as expending polymers such as modified starches. For many disposable absorbent products the adsorbent material is enclosed between a water permeable layer which lies next to the skin and a water impermeable membrane. Examples of such devices are given in the following patents which are included herein by reference U.S. Pat. No. 3,967,623; U.S. Pat. No. 4,226,237 and U.S. Pat. No. 4,333,463 all describe absorbents and articles for adsorbing liquids from the body. U.S. Pat. No. 5,246,433 describes toddler training pants; while U.S. Pat. No. 4,253,461 describes incontinence articles; and WO 93/12745; EP 523683; U.S. Pat. No. 4,583,980 and U.S. Pat. No. 5,962,106 all describe female sanitary products.

Talcum Powders

High intensity fragrance may advantageously be used in talcum powder or other finely divided powder products used for dusting the body. U.S. Pat. No. 1,936,845 describes a powder which may be applied to the body to absorb water while U.S. Pat. No. 5,683,706 teaches that fragranced talcum powder may absorb less water. U.S. Pat. No. 5,861,144 teaches a powder product containing cyclodextrin and a fragrance to reduce malodor.

Wipes Substrates

Liquid compositions incorporating fragrances of the invention can be dispersed on a tissue, a wipe, towel, towelette, and the like. The material may be flushable. As used herein, by “flushable” is meant that the material will pass through at least 10 feet of waste pipe in two toilet flushes. The material may also be biodegradable.

Materials that can be used can be mono or multi-layered, woven or non woven. They can be made of one or of several materials. Preferred are non-woven materials that have a web structure of fibrous or filamentous nature, in; which the timbres or filaments are distributed randomly or with a certain degree of orientation, the former being obtainable by air-laying or by certain wet-laying processes, the latter by other wet-laying or by carding processes. The timbres or filaments can be natural, for example wood pulp, wool, cotton, linen and the like, or synthetic, for example polyvinyls, polyesters, polyamides and the like.

Typically they have a basis weight in the range of 10 to 80 $g/m^2$, in particular of 40 to 70 $g/cm^2$. Particularly preferred materials are of the non-woven type. Based on the raw material that has been used, different types of products can be distinguished.

A first type of carrier is paper based. The raw materials for these carriers are made almost exclusively of cellulose-based fibers or filaments from plant sources (pulp). These can be available from fresh wood-shavings or from recycled material (recycled paper). In a number of wipe applications, such as baby wipes, wipes for cleansing, feminine hygiene wipes, wet paper towels and the like, high wet strength or firmness of non-woven web is a desirable attribute. This can be achieved by the addition of binding materials. Examples of such materials are the so-called wet strength resins. In some cases further additives are incorporated in order to increase the softness of the end product.

In a second type the carrier web is made mainly of staple fibers, e.g. based on cotton, wool, linen synthetic fibers and the like.

Commercial products are made of cellulose fibers, synthetic fibers or mixtures of both. Polyester and polypropylene are known as suitable polymers for the preparation of synthetic fibers. Also in these products, binders can be used to increase the firmness of the non-woven fabric. Webs of increased strength can be obtained by using the so-called spunlace or hydro-entanglement technique. In this technique the individual fibers are twisted together so that an acceptable strength or firmness is obtained without using binding materials. An advantage of the latter technique is the excellent softness of the non-woven material.

Non-woven materials that are made of a mixture of pulp and staple are also known. Such materials are available with binding materials, in particular those mentioned above, or without binding materials. In the latter instance the non-woven is preferably made by the spunlace or hydro-entanglement procedure.

The substrates are wetted with a liquid composition. These can be water-based formulations, in particular they can take the form of aqueous solutions or emulsion-based. These emulsion compositions, which are also referred to as ‘lotions’, preferably are of aqueous nature. The emulsions can be oil-in-water or water-in-oil emulsions, or be of more complex nature such as water-in-oil-in-water. The emulsions may be made by methods known in the art, including the known phase invention technique which is preferred for making fine droplet emulsions. Examples and manufacturing processes for phase invention emulsions are described in WO00/004230.

Aqueous solutions or emulsions containing fragrances of the invention are dosed onto the substrates at a rate between 100 $g/m^2$ and 175 $g/m^2$ of substrate.

The invention will now be explained further by the following non limiting examples.

EXAMPLES

The following are non-limiting examples of fragrance compositions of the invention:

Example 1

Fragrance A is a floral fragrance composition according to the invention, suitable for personal care products. Fragrance A comprises 100% of category a) ingredients.

TABLE 3

Fragrance A

| Ingredient | % (by weight) |
|---|---|
| Cis-3-hexenol | 34.5 |
| Cis-3-hexenyl acetate | 24.1 |
| Isoamyl acetate | 6.9 |
| Ethyl 2-methyl butyrate | 25.9 |
| Ethyl butyrate | 8.6 |

Example 2

Fragrance B is an oriental fragrance composition according to the invention, suitable for personal care products. Fragrance B comprises 100% of category a) ingredients.

TABLE 4

| Fragrance B | |
|---|---|
| Ingredient | % (by weight) |
| Anisic aldehyde | 39.2 |
| Benzyl acetate | 14.7 |
| Cis-3-hexenol | 4.9 |
| 2-Phenylethyl acetate | 29.4 |
| Decalactone gamma | 6.9 |
| Benzaldehyde | 2.9 |
| Vanillin | 2.0 |

Example 3

Fragrance C is an almond fragrance according to the invention. Fragrance C comprises 82% of category a) ingredients.

TABLE 5

| Fragrance C | |
|---|---|
| Ingredient | % (by weight) |
| Anisic aldehyde | 60 |
| Benzyl acetate | 15 |
| Undecalactone gamma | 18 |
| Benzaldehyde | 1 |
| Vanillin | 6 |

Example 4

Fragrance D is a berry fruit fragrance according to the invention which is suited for a personal care product. Fragrance D comprises 100% of category a) ingredients.

TABLE 6

| Fragrance D | |
|---|---|
| Ingredient | % (by weight) |
| Anisic aldehyde | 39.2 |
| Cis-3-hexenol | 29.4 |
| Cis-3-hexenyl acetate | 14.7 |
| Isoamyl acetate | 4.9 |
| Isobutyl acetate | 4.9 |
| Ethyl butyrate | 2.0 |
| Hexyl acetate | 4.9 |

Example 5

Fragrance E is a floral fragrance according to the invention which is suited for a personal care product. Fragrance E comprises 5.24% of an essential oil, 10.5% of a category c) material (nerolidol) and 84.26% of category a) ingredients.

TABLE 7

| Fragrance E | |
|---|---|
| Ingredient | % (by weight) |
| Amyris oil | 5.24 |
| Anisic aldehyde | 21.00 |
| Benzyl acetate | 15.67 |
| Decalactone gamma | 5.22 |
| Geranyl acetate | 10.5 |
| Cis-3-hexenyl propionate | 0.10 |
| Methyl benzoate | 0.42 |
| 2-Phenylethyl acetate | 31.35 |
| Nerolidol | 10.5 |
| Hexyl acetate | 4.9 |

Example 6

Fragrance F is a fruity apple fragrance according to the invention which is suited for a personal care product. Fragrance F comprises 100% of category a) ingredients.

TABLE 8

| Fragrance F | |
|---|---|
| Ingredient | % (by weight) |
| Anisic aldehyde | 37.2 |
| Cis-3-hexenol | 29.4 |
| Trans-2-hexenal | 2.0 |
| Cis-3-hexenyl acetate | 14.7 |
| Isoamyl acetate | 4.9 |
| Isobutyl acetate | 4.9 |
| Ethyl butyrate | 2.0 |
| Hexyl acetate | 4.9 |

Example 7

Fragrance G is an oriental floral fragrance composition according to the invention which is suited for a personal care product. Fragrance G comprises 95% of category a) ingredients and 5% of a category b) material.

TABLE 9

| Fragrance G | |
|---|---|
| Ingredient | % (by weight) |
| Anisic aldehyde | 34.2 |
| Benzaldehyde | 2.9 |
| Benzyl acetate | 14.7 |
| Cis-3-hexenol | 4.9 |
| Phenylethyl acetate | 29.4 |
| Decalactone gamma | 6.9 |
| Vanillin | 2.0 |
| Vetiver oil | 5.0 |

Example 8

Fragrance H is a fruity floral fragrance composition according to the invention which is suited for a personal care product. Fragrance H comprises 100% of category a) ingredients.

TABLE 10

| Fragrance H | |
|---|---|
| Ingredient | % (by weight) |
| Cis-3-hexenyl acetate | 4.0 |
| Ethyl caproate | 4.0 |
| Heliotropine | 20.0 |
| 2-phenylethanol | 40.0 |
| Terpineol alpha | 32.0 |

Example 9

Fragrance I is a berry fruit fragrance according to the invention which is suited for a personal care product. Fragrance I comprises 90% of category a) ingredients and 10% of a category b) material.

TABLE 11

| Fragrance I | |
|---|---|
| Ingredient | % (by weight) |
| Anisic Aldehyde | 42.5 |
| Benzyl acetate | 2.5 |
| Decalactone gamma | 15.0 |
| Patchouli oil | 10.0 |
| Vanillin | 25.0 |
| Veltol ™ | 5.0 |

Example 10

Example 10 is a Shampoo Formulation incorporating fragrance D from example 4.

TABLE 12

| Shampoo Formulation | |
|---|---|
| Ingredient | % (by weight) |
| Lauryl Ether Sulphate | 14.0 |
| Cocoamidopropyl betain | 6.5 |
| Glycerol | 2.0 |
| Sodium N-cocoylamidoethyl N-ethoxycarboxymethylglycinatel | 2.0 |
| Coconut Monoethanolamide | 0.8 |
| Copolymer of dimethyldiallyl ammonium chloride and acylamide | 1.5 |
| Copolymer of acrylic acid and steary methacrylate | 0.3 |
| Salicylic Acid | 0.2 |
| Sodium Benzoate | 0.5 |
| Disodium Ethylene diamine tetra-acetate | 0.25 |
| Fragrance D of example 4 | 0.04 |
| Ethylene glycol distearate | 0.2 |
| Ph adjust with citric acid solution or Sodium hydroxide solution | To pH 5.2 |
| Water | To 100 |

Example 11

A leave-on facial emulsion composition containing a cationic hydrophobic surfactant is prepared by combining the following components utilizing conventional mixing techniques with fragrance B of example 2.

TABLE 13

| Face lotion | |
|---|---|
| Ingredient | % (by weight) |
| Water to | 10.00 |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.20 |
| Fragrance B of example 2 | 0.04 |
| Carbomer 1342 ™ | 0.125 |
| Tetrasodium EDTA | 0.10 |
| DMDM Hydantoin | 0.10 |
| Carbomer 951 ™ | 0.075 |

Example 12

Example 12 is an aqueous skin cleansing liquid for impregnating a non woven textile to from a moist wipe which contains fragrance A of example 1.

TABLE 14

| Skin Cleansing Liquid For Wipe | |
|---|---|
| Ingredient dosage | % (by weight) |
| Propylene Glycol | 0.8 |
| Polysorbate 20 | 1.5 |
| Germaben II ™ | 1.0 |
| Fragrance A of example 1 | 0.02 |
| Silicone antifoam 1510 ™ | 0.015 |
| Lactic acid | To pH 5.4 |
| Water | To 100% |

Germaben II is a commercial preservative from ISP. Various additives could be added to such a formulation for skin benefit such as Aloe vera, DL-panthenol, chamomile extracts in which case the water content would be adjusted to accommodate the additives. Such a liquid would be dosed at around 125 $g/m^2$ on 50 $g/m^2$ spunlace non woven substrate.

Example 13

Example 13 a phase invention emulsion composition containing a fragrance of the invention for impregnating onto a non woven fabric as a moist wipe and incorporating fragrance D of example 4.

TABLE 15

| Skin Cleansing Lotion For Bode Wipe | |
|---|---|
| Ingredient | % (by weight) |
| Emulgade CM ™ | 15 |
| Ceteareth 20 | 4.7 |
| Dicapryl ether | 4.0 |
| Cetearyl isononanoate | 5.0 |
| Cocoglycerides | 2.0 |
| Fragrance D of example 4 | 0.03 |
| Euxyl K702 ™ | 1.0 |
| Tetrasodium EDTA | 0.1 |
| Citric acid | 0.04 |
| Water | To 100% |

Emulgade CM is a concentrated emulsion of cosmetic oils and non-ionic emulsifiers which dilutes into a phase inverted emulsion mixture and is available from Cognis GMBH. Ceteareth 20 is a non-ionic emulsifier. Euxyl K702 is a preservative available from Schüle and Mayr for example 12 various beneficial additives can be incorporated into the formulation which would typically be dosed at around 124 $g/m^2$ on 50 $g/m^2$ spunlace non woven substrate.

Example 14

A Hair Coloration Formulation

The following is a two part formulation for hair coloring brown hair into which fragrances of the invention can be used.

TABLE 16

A Hair Coloration Formulation Part A

| Ingredient | % (by weight) |
|---|---|
| Ceteth-20 | 5 |
| Petrolatum | 5 |
| Beeswax | 2 |
| Steary alcohol | 5 |
| BHT | 0.05 |
| Glycerin | 10 |
| p-aminophenol | 0.3 |
| Resorcinol | 0.2 |
| 4-amono-2-hydroxytoluene | 0.1 |
| Ascorbic acid | 0.3 |
| Disodium EDTA | 0.2 |
| Sodium sulphite | 0.2 |
| Monoethanolamine | 8.1 |
| Fragrance H of example 8 | 0.5 |
| Water | 61.05 |

TABLE 17

A Hair Coloration Formulation Part 2: Hydrogen Peroxide Color Developer

| Ingredient | % (by weight) |
|---|---|
| Ceteth-20 | 5 |
| Paraffinum liquidum | 5 |
| Cetyl alcohol | 0.5 |
| Steareth-20 | 0.5 |
| Hydrogen peroxide (35%) | 17 |
| Water | 72 |

Example 15

Comparative Fragrance J

Fragrance composition J contains 10% of ingredients within category a) of the invention (linalool) and is a conventional fragrance for comparison.

TABLE 18

Comparative Fragrance J

| Ingredient | CAS no | Molecular Wt | ClogP | Boiling pt (° C.) | Bio-Degradable | % (by Weight) |
|---|---|---|---|---|---|---|
| Benzyl Salicylate | 118-58-1 | 228 | 4.16 | 355 | No | 13.00 |
| Dimethyl benzyl carbonyl butyrate | 10094-34-5 | 220 | 4.05 | 285 | No | 1.50 |
| Linalool | 78-70-6 | 154 | 2.75 | 204 | No | 10.00 |
| Ethyl Butylcyclohexyl carbonate | 67801-64-5 | 228 | 4.51 | | | 0.5 |
| Ethyl tricyclodecan-2-carboxylate | 80657-64-3 | 208 | 3.37 | 261 | No | 3 |
| Hexyl Cinnamic Aldehyde | 101-86-0 | 216 | 5.00 | 319 | Yes | 15 |
| Tetrahydro-3-penthyl-2H-pyran-4-yl acetate | 18871-14-2 | 214 | 2.45 | 272 | Yes | 2 |
| Para tert-butyl-alpha Methyl hydrocinnamic Aldehyde | 80-54-6 | 204 | 4.10 | 280 | No | 15 |
| Ethylene brassylate | 105-95-3 | 270 | 3.02 | 434 | Yes | 20 |
| Isobornyl Cyclohexanol | 68877-29-2 | 236 | 5.65 | 313 | No | 20 |

Example 16

Perfume Intensity Test

Fragrance D of example 4 and Comparative Fragrance J of example 15 were compounded and mixed into the shampoo formulation of example 10 at 0.1% by weight and 0.4% by weight respectively. After allowing the products to equilibrate for 24 hours 20 g portions were weighed into 60 mL dark brown glass bottles. In a forced choice triangle test panelists were asked to pick the strongest fragrance; 23 out of 24 panelists chose Fragrance D. This result is statistically significant at greater than 99% confidence interval.

Example 17

Perfume Intensity Test

Fragrance D of example 4 and Comparative Fragrance J of example 15 were compounded and mixed into the shampoo formulation of example 10 at 0.04% by weight and 0.4% by weight respectively. After allowing the products to equilibrate for 24 hours 20 g portions were weighed into 60 mL dark brown glass bottles. In a forced choice triangle test panelists were asked to pick the strongest fragrance; 21 out of 24 panelists chose Fragrance D. This result is statistically significant at greater than 99% confidence interval.

Example 18

Comparative Fragrance K

Fragrance K contains 28.72% of ingredients within category a) of the invention and is a conventional fragrance for comparison.

TABLE 19

Comparative Fragrance K

| Ingredient | CAS no | Molecular Wt | ClogP | Boiling pt (° C.) | Bio-Degradable | % (by Weight) |
|---|---|---|---|---|---|---|
| Undecelenic aldehyde | 112-45-8 | 168 | 4.05 | 233 | Yes | 0.04 |
| Dodecanal | 112-44-7 | 184 | 5.07 | 235 | Yes | 0.04 |
| Benzyl acetate | 140-11-4 | 150 | 1.96 | 216 | Yes | 4.00 |
| Cresyl methyl ether | 104-93-8 | 122 | 2.56 | 170 | Yes | 0.05 |
| Dihydroeugenol | 2785-87-7 | 166 | 2.88 | 265 | No | 0.10 |
| Ethyl acetoaceteate | 141-97-9 | 130 | 0.33 | 169 | Yes | 0.10 |
| 2-isobutyl-4-methyltetrahydro-2H-pyran-4-ol | 63500-71-0 | 172 | 2.16 | 229 | No | 5.00 |
| Methyldihydrojasmonate | 24851-98-7 | 226 | 2.91 | 309 | Yes | 14.9 |
| Piperonal | 120-57-0 | 150 | 1.76 | 257 | Yes | 2.00 |
| Hexyl salicylate | 6259-76-3 | 222 | 4.98 | 328 | Yes | 16.0 |
| Alpha ionone | 127-41-3 | 192 | 3.71 | 259 | No | 0.75 |
| Linalool | 78-70-6 | 154 | 2.75 | 204 | No | 4.50 |
| Linalyl acetate | 115-95-7 | 196 | 3.70 | 228 | No | 4.50 |
| Methyl benzoate | 93-58-3 | 136 | 2.11 | 196 | Yes | 0.02 |
| Gamma methyl ionone | 127-51-5 | 206 | 4.02 | 272 | No | 5.00 |
| Ethylene brassylate | 105-95-3 | 270 | 3.02 | 434 | Yes | 15.00 |
| 2-Phenylethanol | 60-12-8 | 122 | 1.33 | 225 | Yes | 12.00 |
| Isobornyl cyclohexanol | 6877-29-2 | 236 | 5.65 | 313 | No | 15.00 |
| Vanillin | 121-33-5 | 152 | 1.28 | 274 | Yes | 1.00 |

Example 19

Perfume Intensity Test

Fragrance A of example 1 and Comparative Fragrance K of example 18 were compounded and mixed into the shampoo formulation of example 10 at 0.1% by weight and 0.4% by weight respectively. After allowing the products to equilibrate for 24 hours 20 g portions were weighed into 60 mL dark brown glass bottles. In a forced choice triangle test panelists were asked to pick the strongest fragrance; 22 out of 24 panelists chose Fragrance A. This result is statistically significant at greater than 99% confidence interval.

Example 20

Perfume Intensity Test

Fragrance A of example 1 and Comparative Fragrance K of example 18 were compounded and mixed into the shampoo formulation of example 10 at 0.04% by weight and 0.4% by weight respectively. After allowing the products to equilibrate for 24 hours 20 g portions were weighed into 60 mL dark brown glass bottles. In a forced choice triangle test panelists were asked to pick the strongest fragrance; 21 out of 24 panelists chose Fragrance A. This result is statistically significant at greater than 99% confidence interval.

The invention claimed is:

1. An adsorbent article comprising a high intensity fragrance composition which comprises by weight:

a) 75% to 100% of from 4 to 7 fragrance ingredients where each fragrance ingredients consist of at least one kind of atoms selected from the group consisting of a carbon atom, a hydrogen atom, an oxygen atom and a nitrogen atom, comprise an ester functional group, an alcohol functional group or an aldehyde functional group;

have boiling points between 100° C. and 300° C. at a pressure of 760 mm of mercury;

have molecular weights within the range of 70 atomic mass units to 175 atomic mass units, have ClogP values between 0.00 and 4.00;

b) 0 to 25% of an essential oil; and c) 0 to 25% of a fragrance ingredient other than the fragrance ingredients in the above category a), wherein the sum of a), b) and c) equals 100%, and which is hypoallergenic, and in which the fragrance ingredients in category a) are selected from the group consisting of: isoamyl acetate, anisic aldehyde, ethyl butyrate, hexyl acetate, cis-3-hexenol, cis-3-hexenyl acetate, and isobutyl acetate.

2. The adsorbent article according to claim 1, wherein 80 to 100% by weight of the high intensity fragrance composition are ingredients selected from the group consisting of: anisic aldehyde, isobutyl acetate, ethyl butyrate, hexyl acetate, cis-3-hexenol, cis-3-hexenyl acetate, and isoamyl acetate.

3. The adsorbent article according to claim 1, wherein 50 to 100% by weight of the fragrance ingredients in category a) are ingredients selected from the group consisting of: anisic aldehyde, ethyl butyrate, hexyl acetate, cis-3-hexenol, cis-3-hexenyl acetate, and isoamyl acetate.

4. The adsorbent article according to claim 1, wherein 90 to 100% by weight of combined ingredients of the fragrance ingredients in category a) and fragrance ingredient in category c) have boiling points between 100° C. and 250° C. at a pressure of 760 mm of mercury.

5. The adsorbent article according to claim 1, wherein the high intensity fragrance composition has a fruity or floral odor note.

6. An adsorbent article comprising a high intensity fragrance composition which comprises by weight:

a) 75% to 100% of from 4 or 5 fragrance ingredients where each fragrance ingredients consist of at least one kind of atoms selected from the group consisting of a carbon atom, a hydrogen atom, an oxygen atom and a nitrogen atom, comprise an ester functional group, an alcohol functional group or an aldehyde functional group;

have boiling points between 100° C. and 300° C. at a pressure of 760 mm of mercury;

have molecular weights within the range of 70 atomic mass units to 175 atomic mass units, have ClogP values between 0.00 and 4.00;

b) 0 to 25% of an essential oil; and c) 0 to 25% of a fragrance ingredient other than the fragrance ingredients in the above category a), wherein the sum of a), b) and c) equals 100%, and which is hypoallergenic, and wherein the fragrance ingredients in category a) are selected from the group consisting of cis-3-hexenol, cis-3-hexenyl acetate, isoamyl acetate, ethyl 2-methyl butyrate and ethyl butyrate.

7. The adsorbent article according to claim 6, wherein 80 to 100% by weight of the high intensity fragrance composition are ingredients selected from the group consisting of: cis-3-hexenol, cis-3-hexenyl acetate, isoamyl acetate, ethyl 2-methyl butyrate and ethyl butyrate.

8. The adsorbent article according to claim 6, wherein 90 to 100% by weight of combined ingredients of the fragrance ingredients in category a) and fragrance ingredient in category c) have boiling points between 100° C. and 250° C. at a pressure of 760 mm of mercury.

9. The adsorbent article according to claim 6, wherein the high intensity fragrance composition has a fruity or floral odor note.

* * * * *